(12) United States Patent
Izadyar

(10) Patent No.: US 11,965,179 B1
(45) Date of Patent: Apr. 23, 2024

(54) LASER TREATED PLATELET PRODUCT

(71) Applicant: Fariborz Izadyar, Irvine, CA (US)

(72) Inventor: Fariborz Izadyar, Irvine, CA (US)

( * ) Notice: Subject to any disclaimer, the term of this patent is extended or adjusted under 35 U.S.C. 154(b) by 112 days.

(21) Appl. No.: 17/353,388

(22) Filed: Jun. 21, 2021

Related U.S. Application Data

(60) Provisional application No. 63/041,863, filed on Jun. 20, 2020.

(51) Int. Cl.
| | |
|---|---|
| *C12N 5/078* | (2010.01) |
| *A61K 9/00* | (2006.01) |
| *A61K 35/19* | (2015.01) |
| *C12N 11/04* | (2006.01) |
| *C12N 13/00* | (2006.01) |

(52) U.S. Cl.
CPC .......... *C12N 5/0644* (2013.01); *A61K 9/0019* (2013.01); *A61K 9/0095* (2013.01); *A61K 35/19* (2013.01); *C12N 11/04* (2013.01); *C12N 13/00* (2013.01); *C12N 2509/00* (2013.01); *C12N 2529/00* (2013.01)

(58) Field of Classification Search
CPC ...... C12N 5/0644; C12N 11/04; C12N 13/00; C12N 2509/00; C12N 2529/00; A61K 9/0019; A61K 9/0095; A61K 35/19
See application file for complete search history.

(56) References Cited

U.S. PATENT DOCUMENTS

2010/0196497 A1* 8/2010 Lim ................. A61K 35/16 424/530
2021/0128626 A1* 5/2021 Gilbertie ............ A61K 35/15

OTHER PUBLICATIONS

Jooybar et al, Acta Biomaterialia 83 (2019) 233-234). (Year: 2019).*
CellTherapy:Tools "Canine Quick-Spin PRP Kit Instruction Manual" Jun. 2020 (Year: 2020).*

* cited by examiner

*Primary Examiner* — Jeremy C Flinders
*Assistant Examiner* — Thomas R. Amick
(74) *Attorney, Agent, or Firm* — Plager Schack LLP; Mark H. Plager; Kara Verryt

(57) ABSTRACT

A method of creating a pooled platelet lysate product may include obtaining whole blood from a source; separating platelets from the whole blood using a pressurized rotating microfluidic filtration system; creating platelet rich plasma (PRP) by concentrating the platelets in plasma and removing red blood cells and white blood cells using centrifugation; centrifuging the PRP, removing the plasma, and re-suspending the PRP in the lactated ringers solution (LRS) to create concentrated PRP (C-PRP); laser activating the C-PRP to create an activated C-PRP product; freezing and thawing the activated C-PRP product at least 3 times, wherein vortexing and sonication are performed after each thaw; and reconstituting the activated C-PRP in a saline to create a platelet lysate product with a known potency.

10 Claims, 9 Drawing Sheets

LASER TREATED PLATELET PRODUCT

RELATED APPLICATION

This application claims priority to provisional patent application U.S. Ser. No. 63/041,863 filed on Jun. 20, 2020, the entire contents of which is herein incorporated by reference.

BACKGROUND

The embodiments described herein relate generally to medical treatments and, more particularly, to a slow release, cell-free, highly pure, laser treated, platelet based product for orthopedic applications.

Osteoarthritis (OA) is characterized by chronic joint inflammation with concurrent joint erosion and destruction. Interleukin (IL)-1β and Interferon gamma (INF-γ) are two important inflammatory mediators associated with the pathogenesis of arthritis. Interleukin 1 mediates bone resorption and cartilage destruction and, to a lesser extent, contributes to joint swelling and inflammation.

Canine OA or degenerative joint disease (DJD) is a degenerative disease of diathrodial joints that occurs in young and old dogs. This disease generally takes years of wear and tear before clinical symptoms manifest; however, some young animals have predisposing conditions, such as hip dysplasia (HD) or elbow dysplasia symptoms, which may manifest as early as 1-2 years old. OA involves cartilage degeneration, fibrillation and loss, inflammation and hyperplasia of the synovial membrane, abnormal proliferation of bone (osteophyte production) and, eventually, exposure of subchondral bone. All of these changes can elicit varying degrees of pain and lameness. To date, treatment options involve medical management, weight management, physical therapy, and nutraceuticals. However, regardless of the management strategy, the disease progresses towards total joint failure. While orthopedic surgical procedures, such as total joint replacement, may be necessary, these surgeries are often invasive and costly.

Platelet rich plasma (PRP) preparations are being used with moderate success to treat OA in humans and in veterinary animals. Such preparations are hindered, however, by PRP's autologous nature and tremendous patient and processing variability. For this reason, there has been increasing interest in the use of platelet lysate preparations instead of traditional PRP. It has been shown that the effect of PRP on reducing inflammation and symptoms of OA is through their secretory cytokines. Platelet lysate preparations are acellular, thereby reducing concerns over immunogenicity, and contain high concentrations of grown factors and cytokines. In addition, platelet lysate preparations can be stored frozen for readily available use.

The chondroprotective effect of platelet lysate in a rat model of induced arthritis is reported to be due to the suppression of TNF-α-induced activation of NF-κB pathway in chondrocytes. Pooled PL therapy increases synoviocyte proliferation and hyaluronic acid production while protecting chondrocytes from synoviocyte-derived inflammatory mediators. A recent equine study revealed that beneficial effects of PL in OA could be attributed to the decreased activity of matrix metalloproteinase 2 (MMP-2), MMP-9, and the increased concentration of glycosaminoglycans (GAGs) and tissue inhibitor of matrix proteinase-1 (TIMP-1). Consequently, PL represents a therapeutic option for canine osteoarthritis (OA), which affects thousands of dogs in the US alone.

Therefore, what is needed is a canine allogenic, platelet-based product for use as an off the shelf, ready to use treatment for canine recipients, wherein the product may mitigate clinical signs associated with OA in dogs. Specifically, the product may mitigate changes caused by inflammatory mediators IL-1β and INF-γ.

SUMMARY

Some embodiments of the present disclosure include a method of creating a pooled platelet lysate product. The method may include obtaining whole blood from a source; separating platelets from the whole blood using a pressurized rotating microfluidic filtration system; creating platelet rich plasma (PRP) by concentrating the platelets in plasma and removing red blood cells and white blood cells using centrifugation; centrifuging the PRP, removing the plasma, and re-suspending the PRP in lactated ringer solution (LRS) to create concentrated PRP (C-PRP); laser activating the C-PRP to create an activated C-PRP product; freezing and thawing the activated C-PRP product at least 3 times, wherein vortexing is performed after each thaw; and reconstituting the activated C-PRP in a saline to create a platelet lysate product.

BRIEF DESCRIPTION OF THE FIGURES

The detailed description of some embodiments of the invention is made below with reference to the accompanying figures, wherein like numerals represent corresponding parts of the figures.

DETAILED DESCRIPTION

Figure 1:
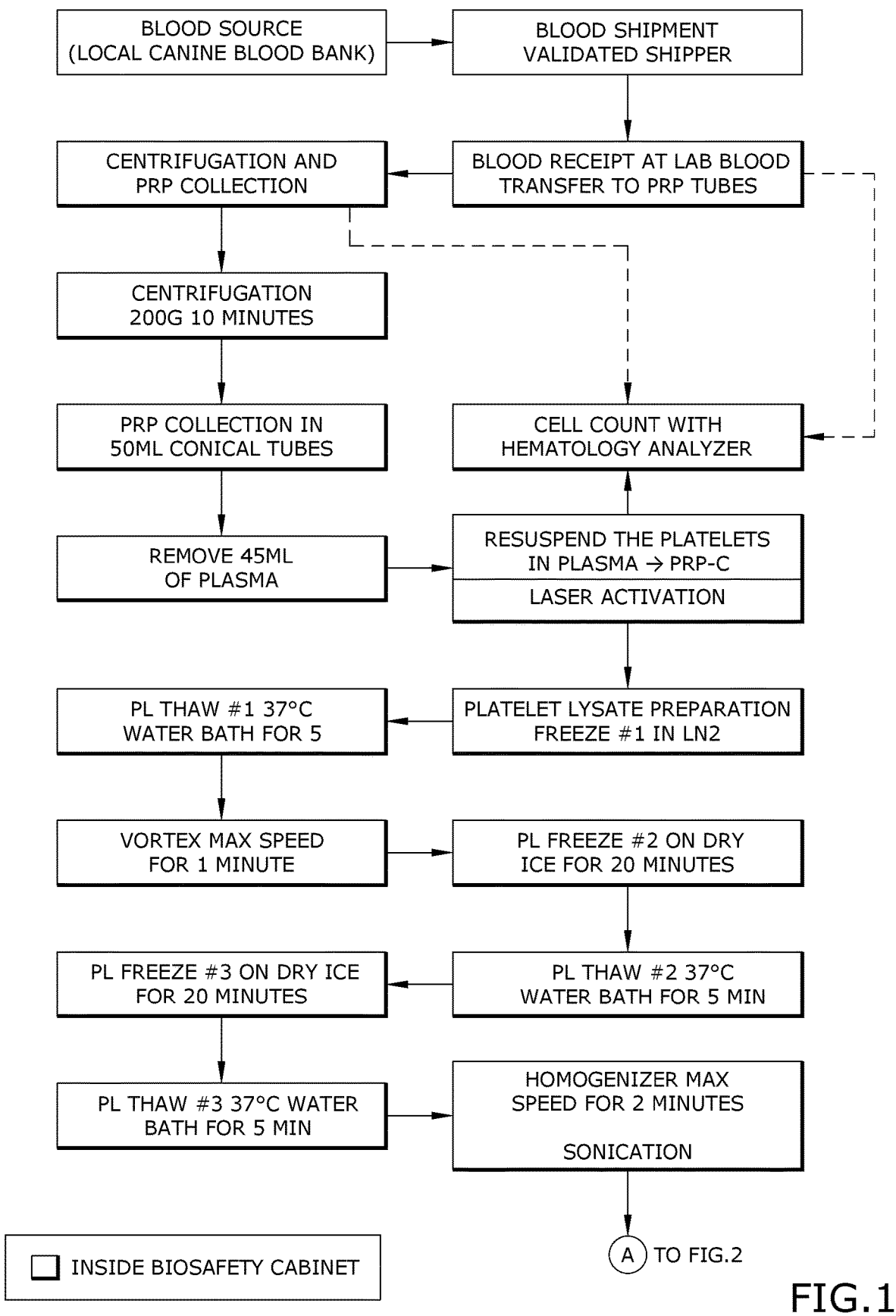
FIG. 1 is a flow diagram describing production of one embodiment of the present disclosure.

In the following detailed description of the invention, numerous details, examples, and embodiments of the invention are described. However, it will be clear and apparent to one skilled in the art that the invention is not limited to the embodiments set forth and that the invention can be adapted for any of several applications.

The composition of the present disclosure may be used as a medicinal treatment and may comprise the following elements. This list of possible constituent elements is intended to be exemplary only, and it is not intended that this list be used to limit the composition of the present application to just these elements. Persons having ordinary skill in the art relevant to the present disclosure may understand there to be equivalent elements that may be substituted within the present disclosure without changing the essential function or operation of the composition.

The various elements of the present disclosure may be related in the following exemplary fashion. It is not intended to limit the scope or nature of the relationships between the various elements and the following examples are presented as illustrative examples only.

By way of example, some embodiments of the invention include a lyophilized pooled platelet lysate for veterinary orthopedic use and wound healing. For example, the product may comprise a cell-free, plasma-free platelet lysate derived product, wherein the platelets are highly pure, activated with a laser, and encapsulated in a biodegradable material, such as collagen or hydrogel, for extended release. The product may be used for orthopedic application, to treat soft tissue damage, such as muscle damage, to accelerate wound healing in patients with open wounds, as eye drops to treat dry eye, and the like. In embodiments, the product may consist of allogeneic canine pooled platelet lysate derived from multiple units of canine blood and formulated to a specified equivalent Cytokine/mL concentration and volume. However, use of other mammal donors, such as humans and equines is envisioned. In embodiments, the platelets may be made of Megakaryocytes derived from induced pluripotent stem (IPS) cells, wherein the IPS cells may be engineered to produce platelets with higher concentrations of cytokines, such as PDGF, TGF-beta, VEGF, and IGF.

In embodiments, a method of preparing the product of the present disclosure may include a method of preparing concentrated platelets without gravity force; a method of preparing decellularized platelet lysate (PL) for allogenic therapy; and methods of lyophilization and encapsulation of PL for extended shelf life. At a top level, the methods comprise obtaining whole blood form a source (i.e., human or animal) using, for example, a pressurized microfluidic system; purifying the platelets from the whole blood and removing other blood cells, such as red blood cells and white blood cells, and then removing the plasma; laser activating the concentrated platelets with low level pulsed laser, causing the platelet granules and their mitochondria to release cytokines and ATP; completing freeze/thaw cycles, such as at least about 3 to 5 freeze/thaw cycles, to destroy the platelet membrane and reconstitute lysate in a lactated ringer solution; encapsulating the lysate in collage beads or hydrogel; and preserving the encapsulated platelet lysate using cryopreservation.

Figure 2:
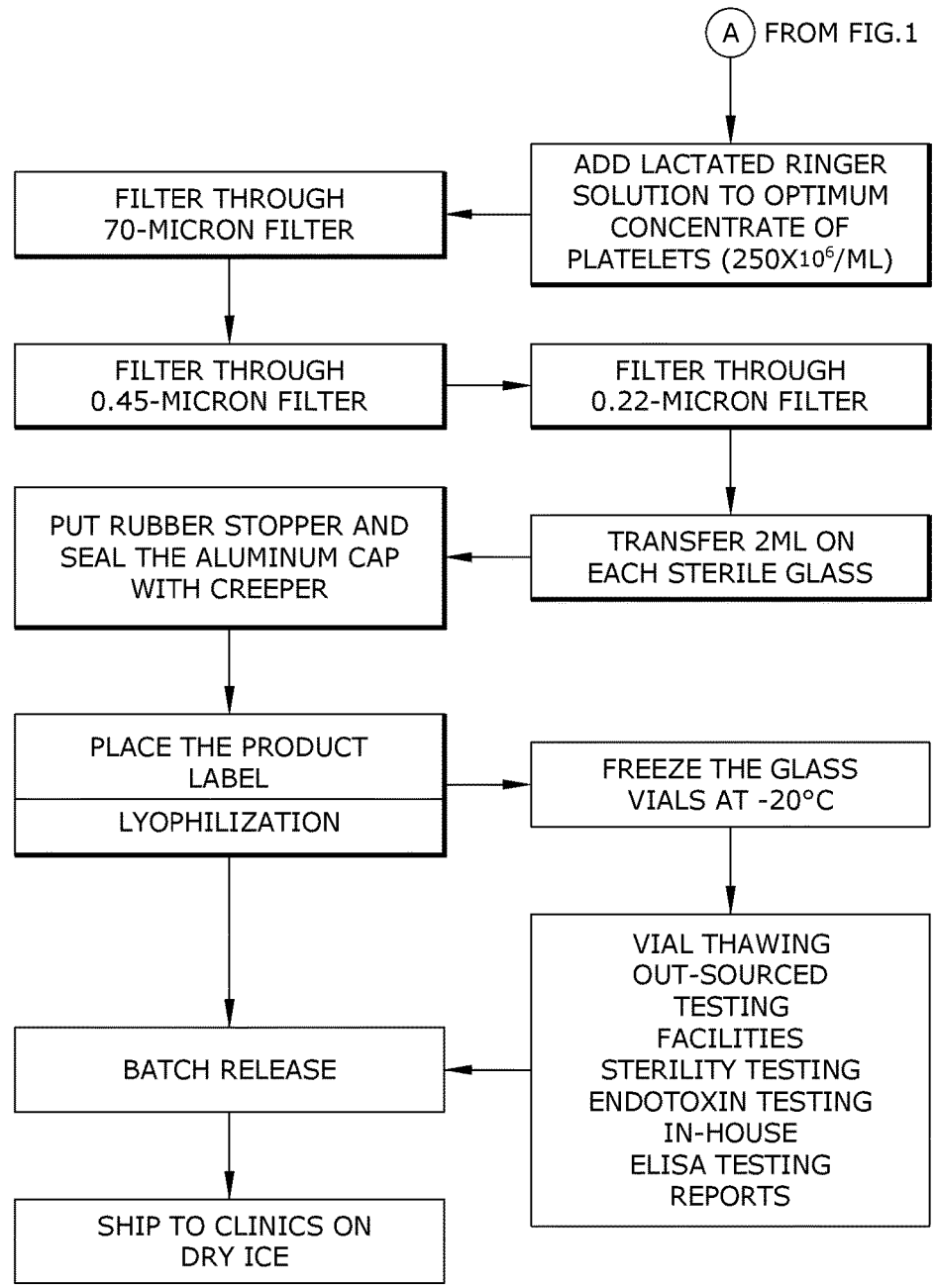
FIG. 2 is a continuation of FIG. 1.
Figure 3:
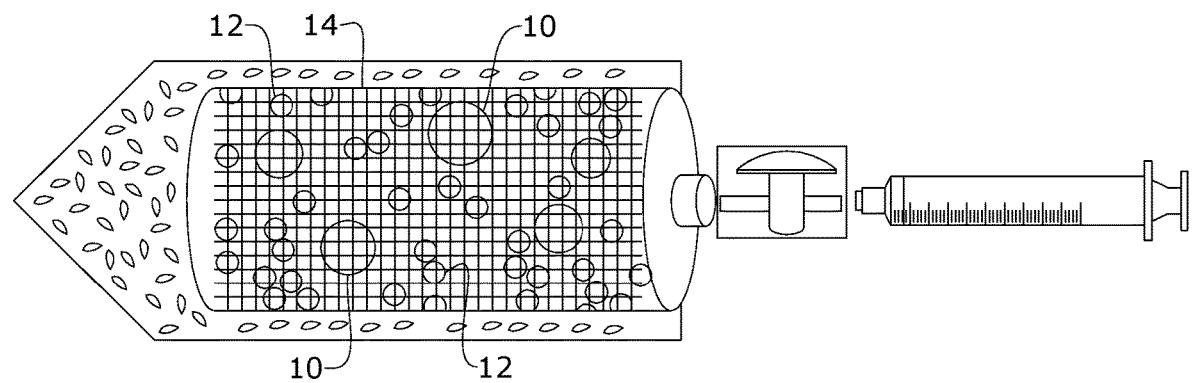
FIG. 3 is an illustration of platelets separation from whole blood.
Figure 4:
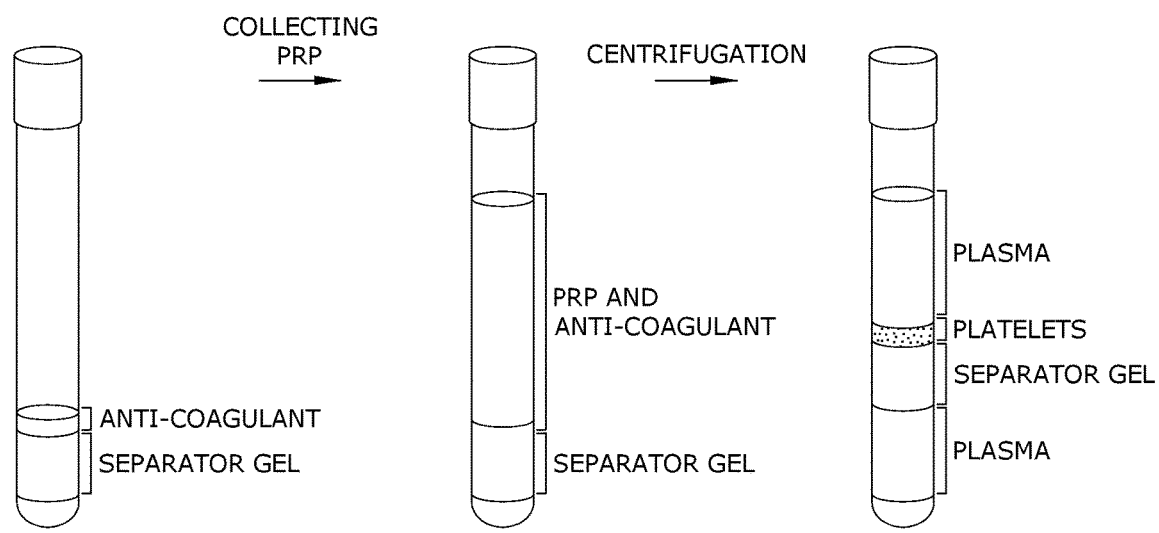
FIG. 4 is an illustration of enrichment of platelets in plasma.
Figure 5:
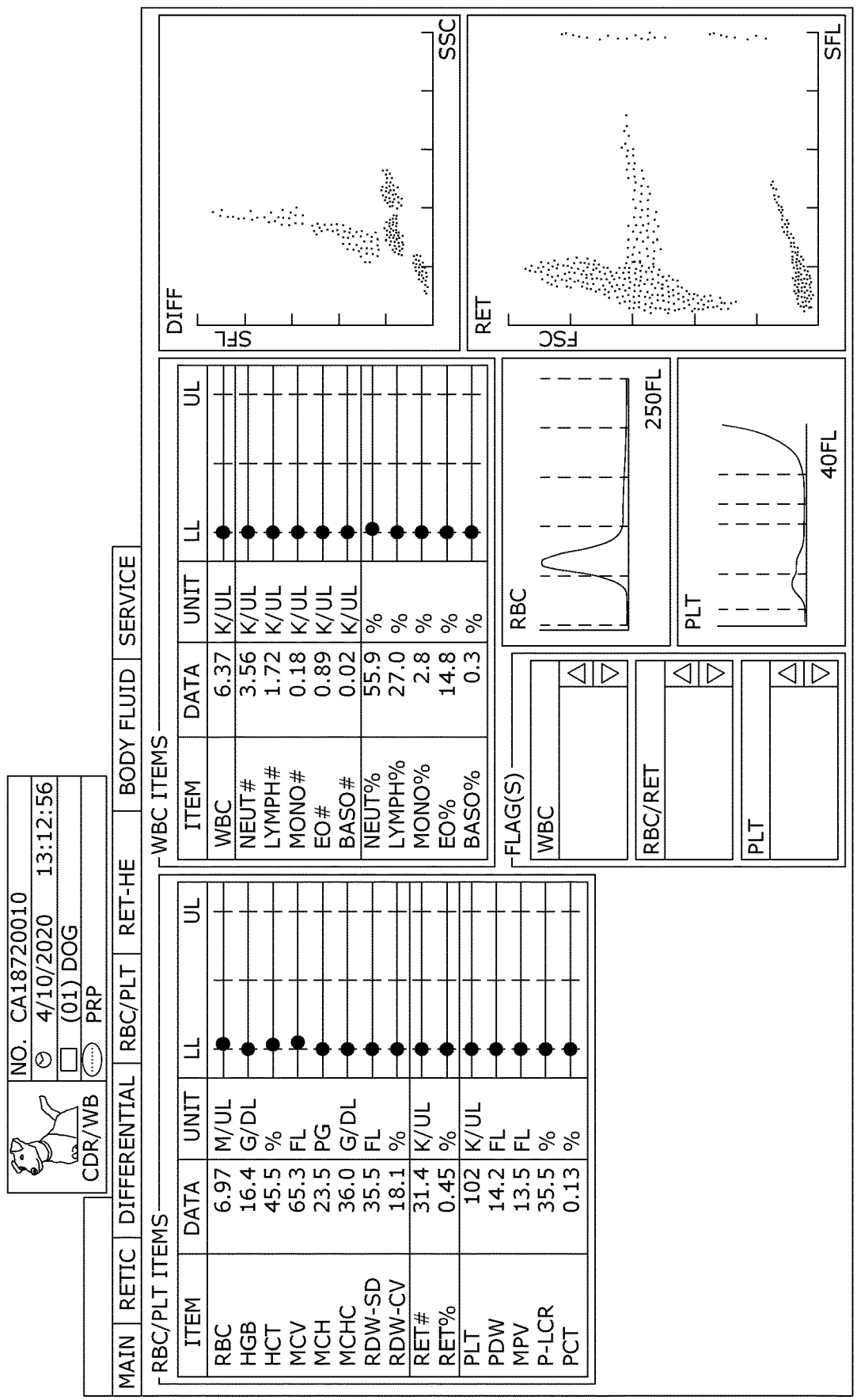
FIG. 5 is a screenshot from a whole blood dot plot analyzer.
Figure 6:
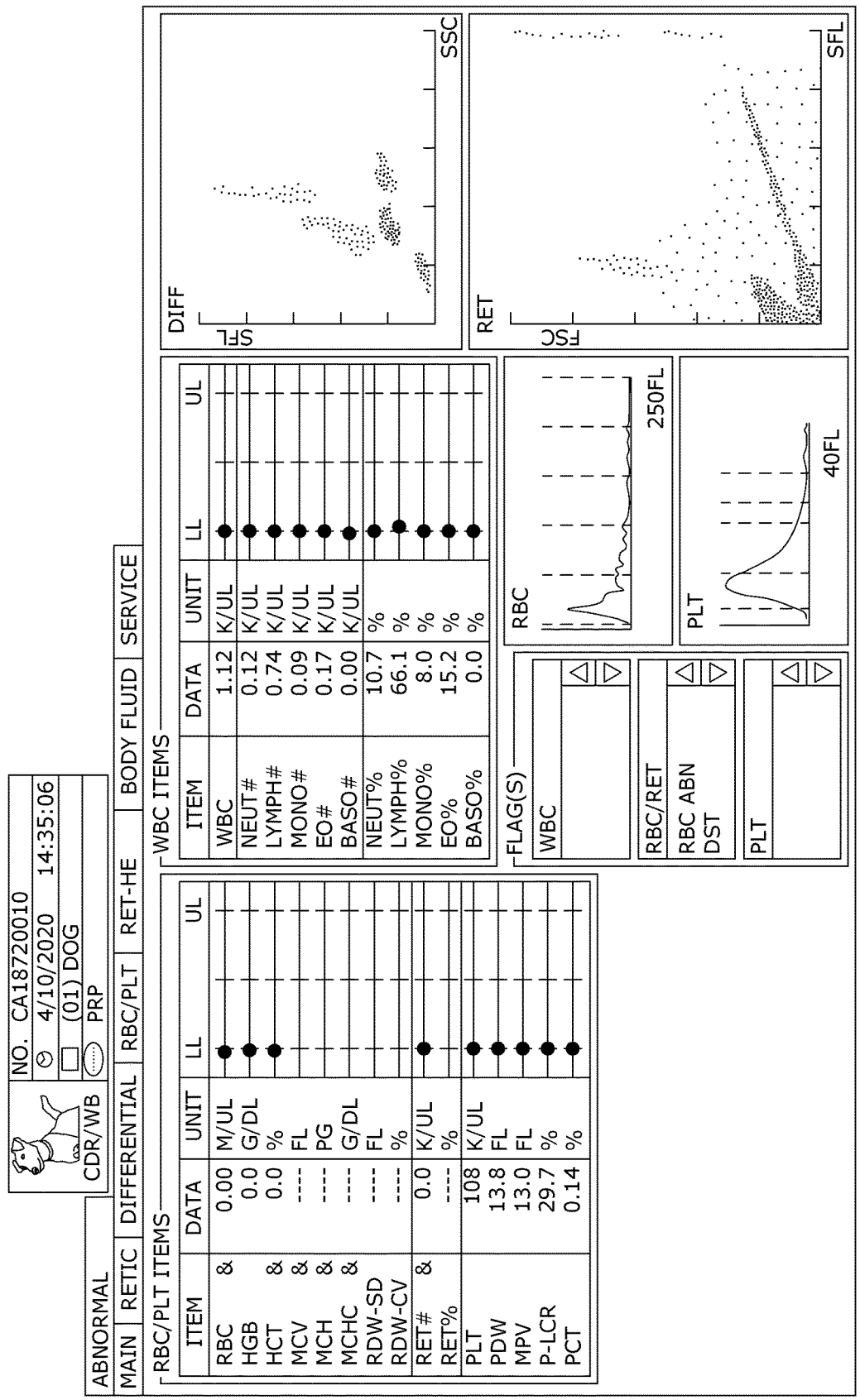
FIG. 6 is a screenshot of a PRP dot plot analyzer.
Figure 7:
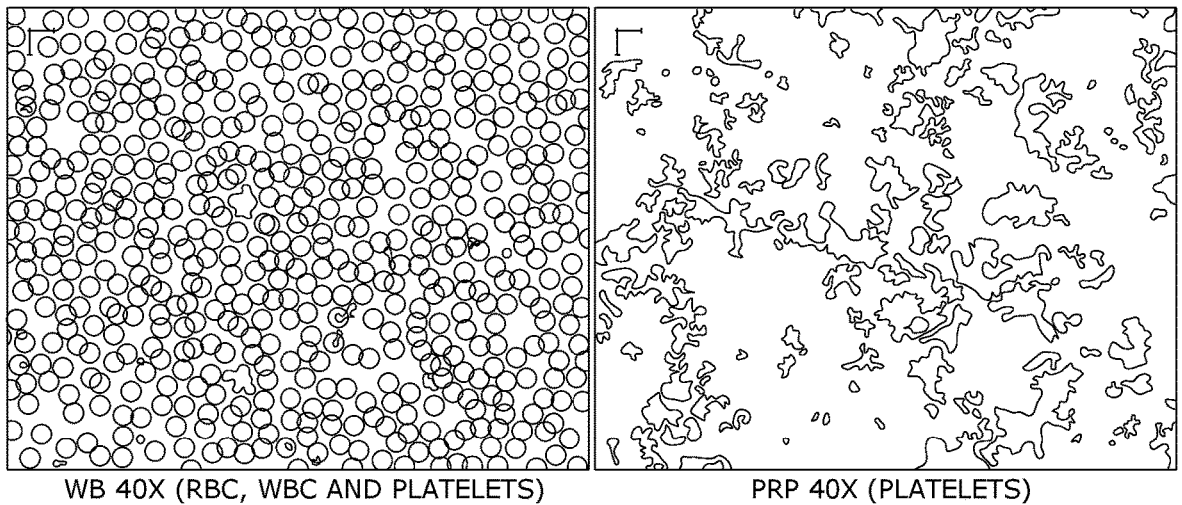
FIG. 7 is an illustration of cells identity in whole blood and concentrated PRP.
Figure 8:
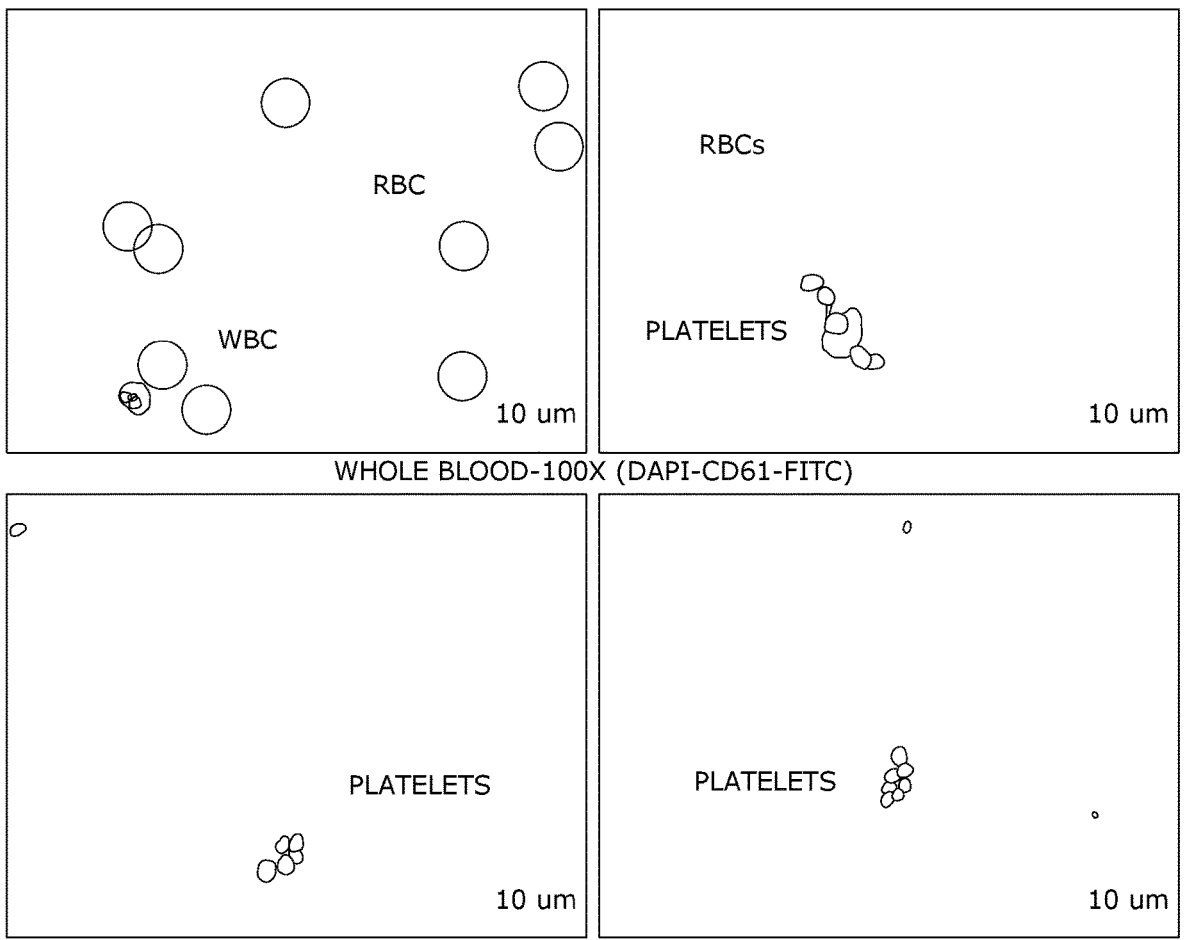
FIG. 8 is an illustration of platelets enriched in PRP.

PRP Preparation and Optimization from Whole Blood: More specifically, as shown in FIGS. 1 and 2, the method of preparing a platelet lysate product may comprise identifying and procuring a blood source, such as animals that have been screened for blood borne pathogens, and whole blood (WB) units with citrate-based anticoagulant may be transferred, via a validated shipper, to the laboratory within 2 hours of collection in, for example, a shipping box with ice pack. As shown in FIG. 3, the platelets 10 may be separated from the whole blood 12 using a pressurized rotating microfluidic filtration system 14. In a biological safety cabinet and under aseptic conditions, a sample of WB may be taken from the blood bag for hematology analyzer to determine the composition of different blood cells. The remaining blood in the blood bag may be transferred into a pressurized rotating microfluidic filtration system followed by a commercially available PRP system, such as Quick-Spin PRP. Using Quick-Spin PRP system may allow for the separation of concentrated platelets in plasma and removing almost all of the red blood cells and the majority of the white blood cells and granulocytes. For small-scale production, 10 mL tubes may be used, while for large-scale manufacturing, larger tubes, such as 30 mL tubes and various speeds (3000 to 4800 rpm) and time (8 to 20 min) may be used. After centrifugation is successful for separation, the red blood cells (RBCs) and a majority of the white blood cells (WBCs) may pass the separation gel, and the platelets may be accumulated on the top of a separation gel, as shown in FIG. 4. Specifically, this separation technique may allow for quick and gentle separation and concentration of the platelets without their activation. The platelets may be re-suspended in the plasma and PRP may be transferred into tubes, such as sterile 50 mL conical tubes. A sample of the PRP may be taken for hematology analyzer to determine the composition of different blood cells in the PRP. In some embodiments, an automated apheresis machine may be used for separation of canine platelets from whole blood. FIGS. 5 and 6 show dot plot and data from an exemplary representative whole blood and PRP samples run through ProCyte hematologic analyzer. As shown in FIG. 7, whole blood contains all blood type cells, while PRP contains mainly platelets as aggregates. The identity of platelets in PRP and whole blood was confirmed by a platelet specific cell surface marker CD61 (FIG. 8).

Figure 9:
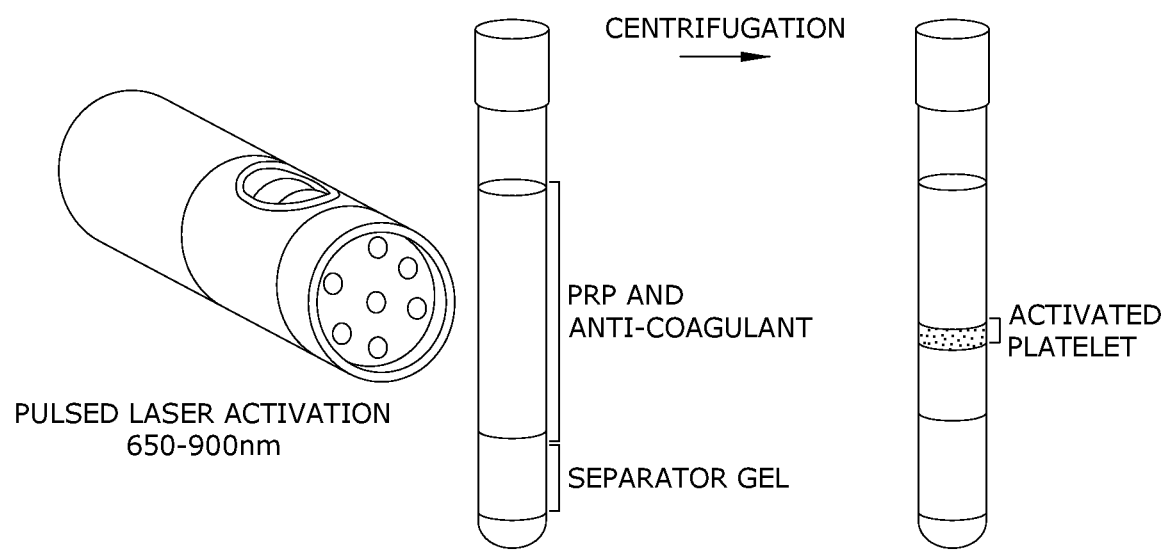
FIG. 9 is an illustration of low-level laser activation.

Platelet Lysate preparation, characterization and specifications: Platelet lysate preparation will be performed in a temperature controlled environment to maintain cold temperature between 2-8° C. In some embodiments, for platelet lysate preparation, the 50 mL conical tubes containing the PRP may be centrifuged at, for example, a speed of about 4800 rpm for a time of, for example, about 10 minutes. At this speed, all of the platelets may be concentrated at the bottom of the tube. After centrifugation, a volume, such as 45 mL, of the plasma will be discarded and platelets will be re-suspended in the remaining 5 mL of plasma. At this stage, the product may be referred to as concentrated PRP (C-PRP). The C-PRP may be laser activated using a low level laser, such as by using a pulsed laser activation at 650 to 900 nm with an intensity of 1-25 j/cm, as shown in FIG. 9. A sample of C-PRP may be taken for hematology analyzer to determine the composition of different blood cells in the C-PRP. The product may then be immediately frozen in liquid nitrogen (LN2). To allow for complete destruction of platelets and release of the cytokines, the product may be thawed and frozen at least two more times with vortexing after each thaw. In some embodiments, the vials may be frozen instantly in liquid nitrogen, while in other embodiments, the vials may be frozen on dry ice for a time of, for example, about 20 minutes. The vials may then be thawed in a water bath at, for example, about 37° C. for a time of, for example, about 5 minutes. Ultrasound force will be applied to destroy the platelets and release their cytoplasmic contents. Vortexing may be done at a maximum speed for about 30 seconds to 1 minute. Depending on the concentration of platelets in the C-PRP, after the last freeze/thaw cycle, a sufficient volume of normal saline may be added so that there is $200\text{-}400 \times 10^6$ platelets in the final product. For example, after the third freezing cycle, the product may be further reconstituted into lactated ringer solution (LRS) to result in a Platelet Lysate (PL) product with a concentration of $250 \times 10^6$ platelets per mL. In embodiments, this may mean that for each 10 mL of whole blood, 1 mL of LRS may be added. Thus, from each unit of blood, about 100-120 mL PRP may be obtained. PL may then be passed through serial filters to remove all the cellular fragments. PL generated from each unit of blood may be combined to create a pooled PL product.

In embodiments, the platelets may be activated before lysate preparation. For example, the platelets may be activated by mechanical, physical, photonic, or electro stimulation or a combination of these activation methods. The freeze/thaw cycles may comprise a series of freeze/thaw cycles using controlled-rate freezer and automated thawing.

After the pooled PL product is obtained, the pooled PL may be subjected to a tissue homogenizer with a preferred speed and time to homogenize the product. For example, the PL may be homogenized for from about 1 to about 10 minutes at a rate of from about 10,000 to about 50,000 rpm. During homogenization, the PL may be kept cold.

The PL may also be decellularized by passing the PL through a series of strainers with different pore sizes, such as those having a size of from about 100 to about 0.22 micron, to remove all the cellular debris from the lysate. Moreover, the PL may be lyophilized for extended stability and shelf life, ease of storage at above freezing temperatures, and transportation.

Determination of the Product Identity: The final Canine Allogeneic Pooled Platelet Lysate (CAPPL) product may contain little or no cells and certain levels of specific cytokines. For determination of cell count, upon arrival of the blood, differential blood cell count may be determined using a veterinary hematology analyzer to set a baseline cell count. After PRP was collected, a sample will be taken and run through the hematology analyzer again. A successful enrichment will be concluded when PRP enriched in platelets and almost all of the RBCs (>99.5%), WBCs (>95%), and granulocytes (>95%) are removed from the PRP. The PRP tubes may be combined and after centrifugation at 2000 to 3000G for about 5 to about 20 min, such as about 10 min, wherein centrifugation may occur from an ultra-cold temperature to room temperature, and removal of most of the plasma (90%), the concentrated platelets may be re-suspended in the remaining plasma, and the product may be referred to concentrated PRP (PRP-C). Samples from PRP-C may be analyzed through the hematology analyzer, and the estimated concentration of platelets in the final product may be determined, wherein the PRP-C should contain more platelets compared to the PRP. After PL preparation, a sample of CAPPL will be taken for cell count analysis, wherein there should be hardly any cells or cell debris in the final product. Microscopic examination may confirm the result of the hematology analyzer, by which PRP should have concentrated platelets and very few other cells, and CAPPL should hardly contain any cell or cellular debris.

Determination of Cytokine Concentration in CAPPL: Important cytokines in PL are PDGF-BB, TGF-beta, FGF, IGF, EGF and VEGF. PDGF is the main cytokine produced by platelets. PDGF-BB is shown to be a strong mitogen and have promotory effect on proliferation of chondrocytes and tenocytes. PDGF-BB concentration of all the CAPPL batches will be measured using a sandwich ELISA kit according to the manufacturer recommendations. FGF, EGF and IGF are also important cytokines within PL mixture with growth promotory and stimulatory properties. TGF-beta is another important cytokine in PL that has anti-inflammatory properties. VEGF, which is also present in PL, is known for angiogenic properties.

Determination of the Product Purity: Blood-borne pathogen testing may be performed on the lysate using PCR-based detection methods. All CAPPL preparations should be negative for aerobic, anaerobic, gram positive, gram negative bacteria, fungi, and yeast and free from blood borne pathogens and has endotoxin level of <0.05 EU/mL.

Immunogenicity and Immune Modulatory Properties of CAPPL: The immunogenicity of CAPPL may be analyzed using an in vitro T cell activation method. This method allows interaction of non-activated T cells with CAPPL and using a T cell activation kit the proportion of activated T cells will be analyzed. The potential immune modulatory property of CAPPL may be analyzed using a Mixed Leukocyte Reaction assay, which may allow interaction of CAPPL with activated T cells in vitro. A reduction in proportion of activated T cell represents the immune modulatory function of the CAPPL. T cell proliferation may be determined by Brdu labeling, and T-cell activation may be determined by a T cell activation kit.

Storage and Stability: Because cytokines within PL may be temperature sensitive, the final product may be frozen immediately and kept frozen until use. The product may be kept at a temperature of from about −196° C. to about 4° C. for a period of from about 1 to about 12 months. In some embodiments, the product may be stable at a temperature of about −20° C. for about 12 months.

Example 1: Canine chondrocytes were collected from the meniscus of a healthy dog. Chondrocytes were cultured in chondrocyte culture media for 6 days in various culture conditions. First, the influence of CCPL on cell morphology, viability and proliferation and matrix production was tested by culturing primary canine chondrocytes in chondrocyte media supplemented with various concentrations of CPPL. Subsequently, the same parameters were determined after stimulation of canine chondrocytes with inflammatory cytokine IL-1B or INF-γ for various time points with or without CPPL. Cell morphology was assessed using light microscopy. Cell viability and proliferation was performed using MTT colorimetric assay and plate reader. Matrix production was determined using Alcian Blue staining and Aggrecan ELISA assay.

Results: Microscopic examination revealed that addition of CPPL resulted in more cells and more clusters of chondrocytes in a dose dependent manner. Similarly, MTT proliferation assay revealed that addition of CPPL to primary cultured canine chondrocytes increased their proliferation. Matrix production by primary canine chondrocytes was also increased by CPPL in a dose dependent manner. Addition of recombinant canine IL-1B or recombinant canine INF-γ reduced cell number and viability as well as chondrocyte proliferation index. Interestingly, supplementation of CPPL blocked the effect of IL-1B or INF-γ on chondrocyte cell death and improved chondrocyte viability and proliferation activity. The results indicate protective effect of CPPL on canine chondrocyte under inflammatory conditions and provide evidence to justify in vivo investigations of CPPL as an adjunct treatment for canine OA.

Example 2 (Preliminary Data): A few units of canine whole blood were obtained from a local animal blood bank, and the protocol for preparation of PL was practiced. Cellular composition of PRP collected from different canine blood and used for preparation of canine allogeneic platelet lysate (CAPL) batches, as detected by hematology analyzer is presented in the following Table 1, wherein WB is whole blood and PRP-C is platelet rich plasma concentrate.

TABLE 1

Blood Cell Composition During Preparation of PRP used for Preparation of PL

| CAPL | Platelets ($\times 10^3/\mu l$) | | RBC ($\times 10^6/\mu l$) | | WBC ($\times 10^3/\mu l$) | | Neutrophils ($\times 10^3/\mu l$) | |
|---|---|---|---|---|---|---|---|---|
| Lot | WB | PRP-C | WB | PRP-C | WB | PRP-C | WB | PRP-C |
| C005-20 | 102 | 1080 | 6.97 | 0.00 | 6.37 | 1.12 | 3.56 | 0.12 |
| C004-20 | 208 | 1760 | 6.39 | 0.01 | 9.03 | 0.59 | 5.43 | 0.06 |
| C003-20 | 178 | 1240 | 7.16 | 0.01 | 7.19 | 1.60 | 4.00 | 0.61 |
| C002-20 | 218 | 1290 | 7.15 | 0.00 | 5.18 | 0.19 | 3.62 | 0.04 |
| C001-20 | 117 | 820 | 7.77 | 0.01 | 6.44 | 0.78 | 3.24 | 0.04 |

In addition to hematology analyzer, a sample of WB and PRP-C was collected and a smear was prepared for staining with wright bloodstain. The number of different blood cells, including platelets, was confirmed using microscopic evaluation and a representative image is shown in FIG. 7. The identity of platelets was confirmed by a platelet specific marker CD61 (FIG. 8).

Determination of PDGF-BB Concentration in CAPL: PDGF-BB concentration of all the CAPL batches was measured using a sandwich ELISA kit according to the manufacturer recommendations. All the batches of CAPL contained variable (3-10 ng/mL) amount of PDGF-BB, as shown in the following Table 2. As shown, there is a variation in concentration of the PDGF-BB in different batches of canine PL.

TABLE 2

PDGF-BB Concentration in different batches of Canine PL

| Platelet Lysate Batch ID | Platelet Number per vial ($\times 10^6$) | PDGF-BB (ng/ml) |
|---|---|---|
| C001-20 | 150 | 3 |
| C002-20 | 160 | 2.3 |
| C003-20 | 330 | 9.8 |
| C004-20 | 240 | 4.5 |
| C005-20 | 400 | 9 |

Effect of CPPL on Chondrocyte Proliferation: Validation data of a batch of CAPL (C003-20) is presented. Canine primary chondrocytes were cultured with two concentrations of CAPL (10% and 50%) and morphology of the cells was analyzed at day 2, 4, and 6 of culture. Addition of CAPL resulted in more cells and more clusters of chondrocytes in a dose dependent manner.

In addition to morphological analysis, MTT colorimetric assay for proliferation was used and the absorbance was measured using a colorimetric plate reader at 490 nm according to the manufacturer recommendations. Similar to morphology, MTT assay confirmed that PL increased proliferation of canine chondrocyte in a dose dependent manner ($P<0.05$).

Effect of CPPL on Glycosaminoglycan Synthesis: To investigate whether addition of CAPL stimulated production of glycosaminoglycans, the cells were stained with Alcian blue, and the plates were analyzed using microscopic examination, wherein the intensity of Alcian blue staining was measured using a plate reader at 620 nm. The microscopic examination of cells at day 7 showed that addition of CAPL to chondrocyte culture medium increased the Alcian blue staining, indicating that more glycosaminoglycans was produced. The intensity of Alcian blue staining was higher in the presence of higher concentration of PL, indicating that PL enhanced GAG production in a dose dependent manner.

Figure 10:
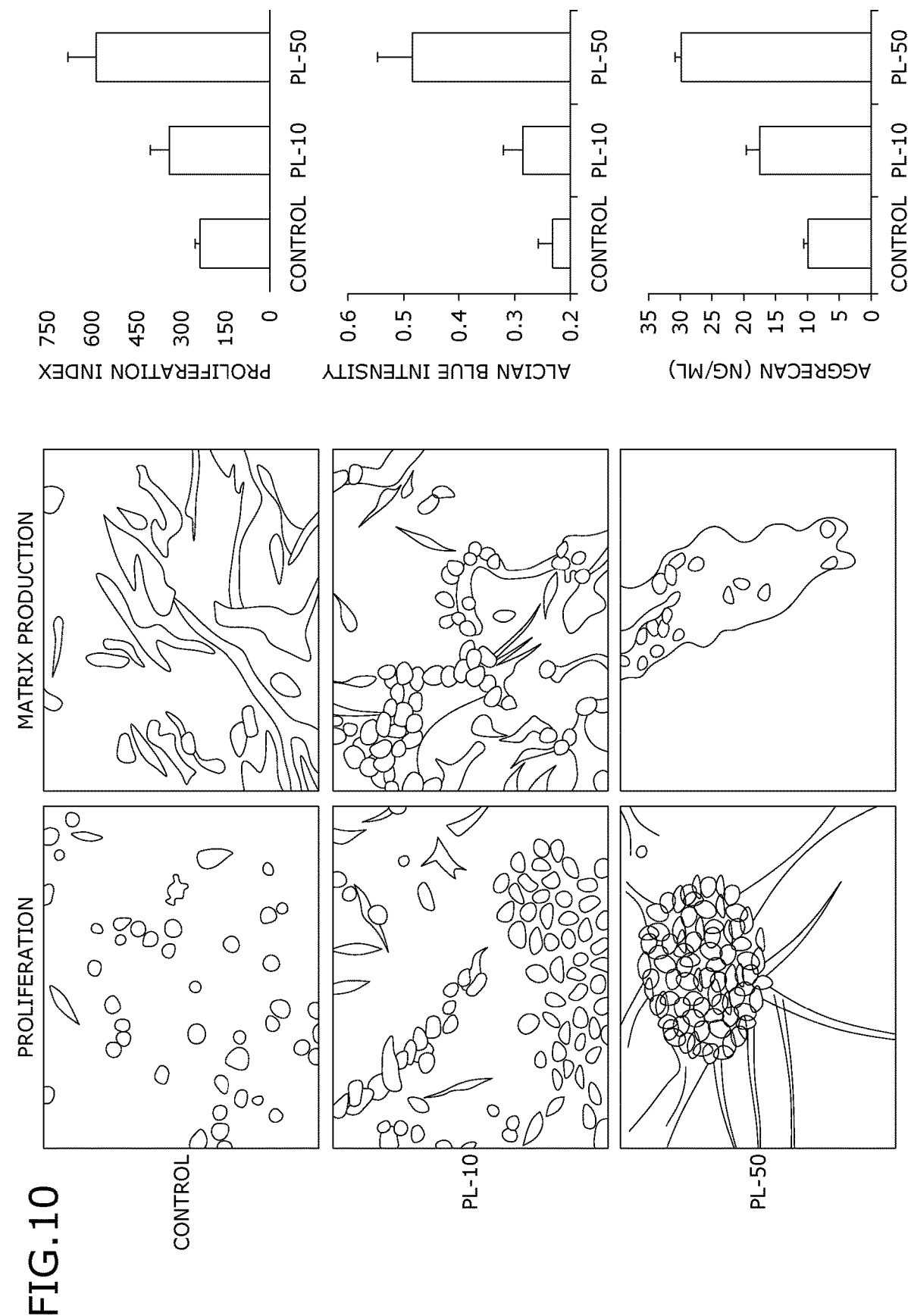
FIG. 10 is an illustration of the effect of canine allogenic platelets.

The morphology of chondrocytes in 2D culture changed after a few days of culture. Analysis of the stained cells with the plate reader also confirmed the microscopic examination and showed that the addition of CAPL to chondrocyte culture medium significantly ($P<0.05$) increased the Alcian blue staining in a dose dependent manner. The resulting data is shown in FIG. 10.

Figure 11:
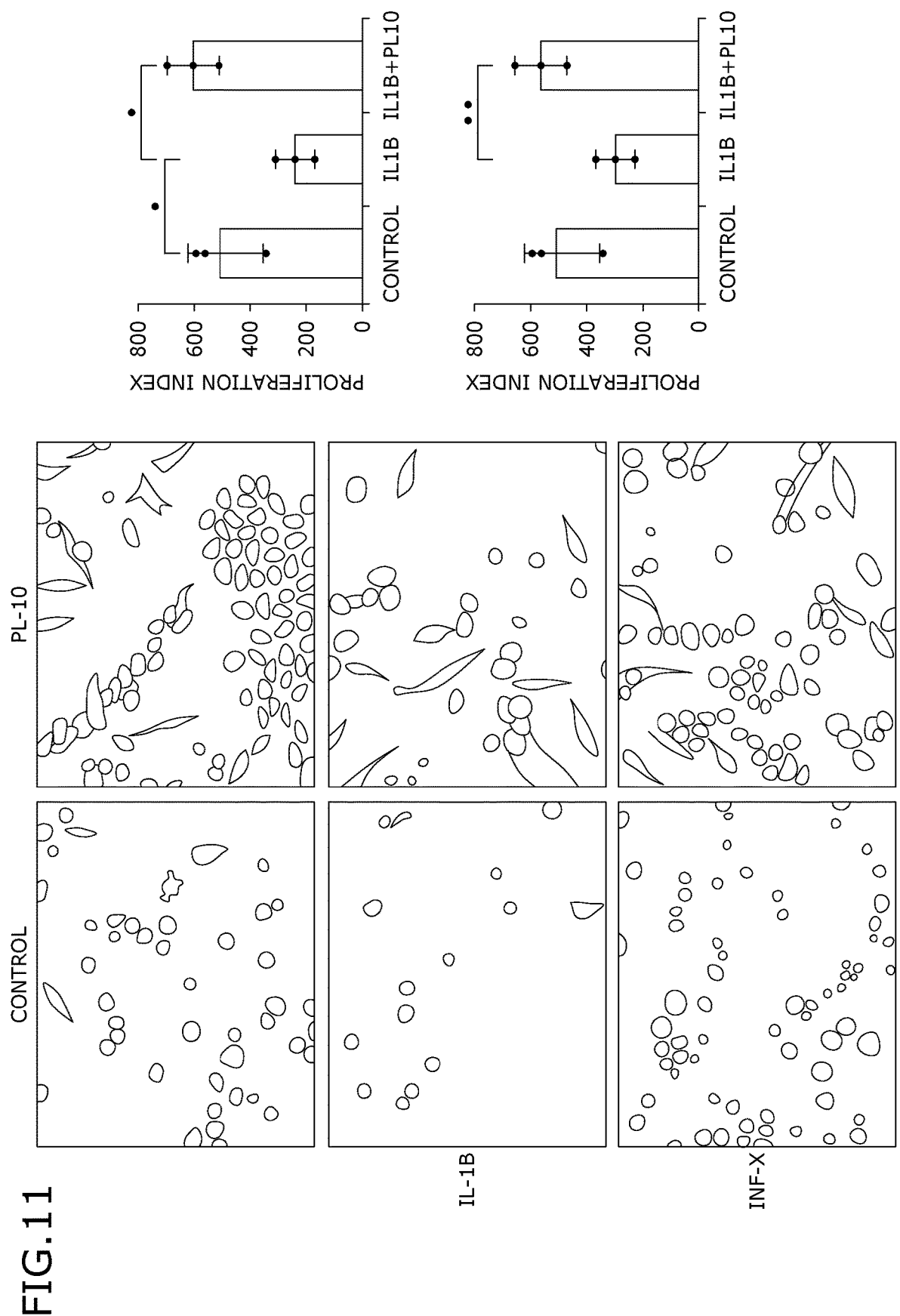
FIG. 11 is an illustration of the chondoprotective effects of an embodiment of the present disclosure.

Protecting effects of CPPL on IL1B or INF-gamma induced cell death: Addition of as low as 1 ng/mL IL1B or INF-gamma to chondrocyte media significantly reduced cell proliferation as determined by MTT colorimetric assay. Supplementation of PL 10% significantly improved cell proliferation of the chondrocytes. The resulting data is shown in FIG. 11.

Application Methods: To use the product of the present disclosure, a therapeutically effective dosage of the product may be delivered to a patient, such as an animal like a dog, in need. The product may be delivered using any suitable or desired application method, which may include, for example, a platelet lysate bandage, a platelet lysate gel applicator, or a pulsed electromagnetic field (PEMF) wound healing device with an insert for PL-gel application.

When it comes to a platelet lysate bandage, the platelet lysate may be provided in a separate vial kept frozen. Alternatively, the PL may be lyophilized and kept at about 4° C., wherein the lyophilized PL may be reconstituted with an isotonic solution prior to administration. A liquid spray applicator may be provided, along with a separate bandage covered by a hydrogel. Prior to application of the bandage to the wound, the wound may be cleaned and debris and dead tissue may be removed. The PL may be thawed and connected to the spray application and sprayed onto the wound. The bandage covered with hydrogel may then be placed on the wound, wherein this procedure may be repeated at a predetermined interval of time, such as about once a week, until granulation tissue is formed.

With respect to a platelet lysate gel applicator, the PL may be provided in a separate vial kept frozen. Alternatively, the PL may be lyophilized and kept at about 4° C., wherein the lyophilized PL may be reconstituted with an isotonic solution prior to administration. Hydrogel liquid and a liquid spray and gel applicator may be provided. Prior to application to the wound, the wound may be cleaned and all debris and dead tissue may be removed. The PL and hydrogel may be inserted into the spray applicator and may be sprayed onto the wound. An appropriate wound dressing may be provided, wherein this procedure may be repeated at a predetermined interval of time, such as about once a week, until granulation tissue is formed.

Regarding the PEMF wound healing device application, a device for application of PEMF with the capability of spraying to the wound will be provided. Different shaped loops for different forms and sizes of wounds may be provided. The PL may be provided in a separate vial kept frozen. Alternatively, the PL may be lyophilized and kept at about 4° C., wherein the lyophilized PL may be reconstituted with an isotonic solution prior to administration. Hydrogel liquid and a liquid spray and gel applicator may be provided. Prior to application to the wound, the wound may be cleaned and all debris and dead tissue may be removed. PL and hydrogel may be inserted into the spray applicator, which may be connected to the PEMF device. The device may be mounted onto the wound area, and an appropriate amount of PEMF and the PL and hydrogel may be applied at a predetermined interval of time, such as every day. An appropriate wound dressing may be provided and applied.

While the above product is described as being used for canines, it is not limited to being used with canine patients. In fact, it may be used for any patient in need. For example, it may be used to treat osteoarthritis, tendinitis or ligament tears, intervertebral disc degeneration, treatment of bone fractures, treatment of chronic open wounds, and the like.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A method of creating a pooled platelet lysate product, the method comprising:
   obtaining whole blood from a source:
   purifying platelets from the whole blood and removing red blood cells, white blood cells, and plasma, thus separating the platelets from the whole blood to create concentrated platelets;
   activating the concentrated platelets, causing the platelets to release cytokines and ATP; and
   treating the activated concentrated platelets with a plurality of freeze/thaw cycles to destroy platelet membranes to create a platelet lysate,
   wherein:
      separating the platelets from the whole blood comprises using a pressurized rotating microfluidic filtration system; and
      the pressurized rotating microfluidic filtration system includes an outer tube surrounding an inner tube and rotating relative to the inner tube, wherein the inner tube is porous and is configured to prevent transfer of larger sized molecules into the outer tube, thus separating the platelets from the whole blood.

2. The method of claim 1, wherein activating the concentrated platelets comprises activating the concentrated platelets with a laser.

3. The method of claim 2, wherein the laser is a low level pulsed laser.

4. The method of claim 1, further comprising encapsulating the platelet lysate in a material selected from the group consisting of collagen beads and hydrogel.

5. The method of claim 4, further comprising preserving the encapsulated platelet lysate using cryopreservation.

6. A method of creating a pooled platelet lysate product, the method comprising:
   obtaining whole blood from a source:
   separating the platelets from the whole blood comprises using a pressurized rotating microfluidic filtration system, the pressurized rotating microfluidic filtration system including an outer tube surrounding an inner tube and rotating relative to the inner tube, wherein the inner tube is porous and is configured to prevent transfer of larger sized molecules into the outer tube, thus separating the platelets from the whole blood,
   creating platelet rich plasma (PRP) by concentrating the platelets in plasma and removing red blood cells and white blood cells using centrifugation;
   centrifuging the PRP, removing a portion of a volume of the plasma, and re-suspending the PRP in the remaining plasma to create concentrated PRP (C-PRP); laser activating the C-PRP to create an activated C-PRP product; freezing and thawing the activated C-PRP product at least 3 times, wherein vortexing is performed after each thaw; and reconstituting the activated C-PRP in a saline to create a platelet lysate product.

7. The method of claim 6, wherein creating the PRP comprises centrifugation performed at a speed of from about 3000 to about 4800 rpm at a time of from about 8 to about 20 minutes.

8. The method of claim 6, wherein laser activation comprising using a pulsed laser at form about 650 to about 900 nm with an intensity of 1 to 25 J/cm$^2$.

9. The method of claim 6, wherein the platelet lysate product has a concentration of about 200-400×10$^6$ platelets per mL.

10. The method of claim 6, further comprising encapsulating the platelet lysate product for extended release in a joint space.

* * * * *